(12) United States Patent
Haslinger (10) Patent No.: US 8,915,528 B2
(45) Date of Patent: Dec. 23, 2014

(54) GRIPPING DEVICE

(75) Inventor: Martin Haslinger, Weiten (AT)

(73) Assignee: Otto Bock Healthcare Products GmbH, Vienna (AT)

( * ) Notice: Subject to any disclaimer, the term of this patent is extended or adjusted under 35 U.S.C. 154(b) by 0 days.

(21) Appl. No.: 13/390,554

(22) PCT Filed: Jul. 20, 2010

(86) PCT No.: PCT/EP2010/004419
§ 371 (c)(1),
(2), (4) Date: Feb. 15, 2012

(87) PCT Pub. No.: WO2011/020535
PCT Pub. Date: Feb. 24, 2011

(65) Prior Publication Data
US 2012/0146352 A1    Jun. 14, 2012

(30) Foreign Application Priority Data

Aug. 19, 2009  (DE) .......................... 10 2009 037 898

(51) Int. Cl.
*B25J 15/08*    (2006.01)
*B25J 15/00*    (2006.01)
*A61F 2/58*    (2006.01)
*B25J 9/10*    (2006.01)
*A61F 2/70*    (2006.01)
*A61F 2/50*    (2006.01)

(52) U.S. Cl.
CPC ........... *A61F 2/586* (2013.01); *A61F 2002/701* (2013.01); *B25J 15/0009* (2013.01); *A61F 2002/5007* (2013.01); *B25J 9/102* (2013.01)
USPC .......................................... 294/106; 623/64

(58) Field of Classification Search
USPC .............. 294/106, 115, 202, 213; 901/38, 39; 623/64
See application file for complete search history.

(56) References Cited

U.S. PATENT DOCUMENTS 1,792,183 A * 2/1931 Pecorella ......................... 623/64
2,493,776 A * 1/1950 Pecorella et al. ............... 623/64

(Continued)

FOREIGN PATENT DOCUMENTS

DE    102007022973 A1    1/2008
DE    102007005858 A1    8/2008

(Continued)

OTHER PUBLICATIONS

Young June Shin et al., Application of Sliding Actuation Mechanism to Robot Finger, IEEE/ASME International Conf. on Advanced Intelligent Mechatronics, Singapore, Jul. 14-17, 2009, pp. 550-553.

(Continued)

*Primary Examiner* — Dean Kramer
(74) *Attorney, Agent, or Firm* — Holland & Hart (57) ABSTRACT

The invention relates to a gripping device, comprising a proximal member (10), a medial member (20), and a distal member (30), which are each pivotably supported on each other, and comprising an actuator (80), which is coupled to a slidably supported coupling element (50), wherein the coupling element (50) is arranged between the proximal member (10) and the distal member (30) and is connected in a force-transmitting manner both to the proximal member (10) and to the distal member (30). According to the invention, at least one lever (40) is arranged on the coupling element (50), which lever is connected both to the proximal member (10) and to the distal member (30) and kinematically couples the proximal member (10) with the distal member (30).

20 Claims, 14 Drawing Sheets

(56) References Cited

U.S. PATENT DOCUMENTS

| | | | |
|---|---|---|---|
| 4,094,016 A | | 6/1978 | Eroyan |
| 4,364,593 A | * | 12/1982 | Maeda ........................ 294/106 |
| 4,834,443 A | * | 5/1989 | Crowder et al. ............. 294/106 |
| 5,941,914 A | * | 8/1999 | Jacobsen et al. ................ 623/64 |
| 6,244,644 B1 | * | 6/2001 | Lovchik et al. ............... 294/111 |
| 6,908,489 B2 | * | 6/2005 | Didrick ........................... 623/64 |
| 7,766,405 B2 | * | 8/2010 | Matsuda et al. ............. 294/106 |
| 8,100,986 B2 | | 1/2012 | Puchhammer et al. |
| 2008/0023974 A1 | | 1/2008 | Park et al. |

FOREIGN PATENT DOCUMENTS

| | | |
|---|---|---|
| EP | 1829650 B1 | 10/2008 |
| WO | 03080297 A1 | 10/2003 |
| WO | 2008092695 A1 | 8/2008 |
| WO | 2008098057 A2 | 8/2008 |

OTHER PUBLICATIONS

International Search Report for PCT International Patent Application No. PCT/EP2010/004419, mailed Nov. 19, 2010.

* cited by examiner

GRIPPING DEVICE

TECHNICAL FIELD

The invention relates to a gripping device, comprising a proximal member, a medial member, and a distal member, which are mounted pivotably on each other, and comprising an actuator, which is coupled to a slidably mounted coupling element, the coupling element being arranged between the proximal member and the distal member and being connected to the proximal member and to the distal member in a force-transmitting manner.

BACKGROUND

Such a gripping device is useful in particular for hand prostheses, in which the gripping device can be used as a prosthetic finger. In addition to applications in prosthetics, it is also possible to use the gripping device in other technical fields, for example in handling technology or in so-called robots.

A gripping device of this type, in the form of a prosthetic finger, is known from DE 10 2007 005 858 A1. A longitudinally movable balance arm is arranged in the medial member and is connected by levers to the proximal member and to the distal member. The attachment of the balance arm to the proximal member and to the distal member via levers is mechanically complex. In addition, it is necessary to encapsulate the medial member with the levers in order to produce a finger ready for use.

SUMMARY

The object of the present invention is to make available a gripping device which is more robust and is easier to produce.

According to the invention, this object is achieved by a gripping device having the features of the main claim. Advantageous embodiments and refinements of the invention are set forth in the dependent claims.

In the gripping device according to the invention, comprising a proximal member, a medial member, and a distal member, which are each mounted pivotably on each other, and comprising an actuator, which is coupled, if appropriate via a gear mechanism, to a slidably mounted coupling element, the coupling element being arranged between the proximal member and the distal member and being connected both to the proximal member and to the distal member in a force-transmitting manner, provision is made that at least one lever is arranged on the coupling element, which lever is connected both to the proximal member and also to the distal member and kinematically couples the proximal member to the distal member. By integrating the force transmission in a lever, it is possible that the individual members can be coupled directly to one another in a simple manner, such that a coordinated gripping movement can be achieved by movement of the coupling member. This means a reduction in the number of parts and a stabilization of the mechanical force transmission chain, such that, in addition to an improvement in economy, it is also possible to ensure a mechanical improvement as a result of an improved stability inside the gripping device. Moreover, the lever can be designed such that it covers the entire medial member, and such that no additional enclosure is needed to protect the mechanisms. Only a lever is still needed to couple the coupling element to the proximal member and to the distal member.

The actuator, which can be designed in particular as a motor but also as a flexible drive, a driven shaft, cardan drive or the like, can drive the coupling element in order to cause the movement of the coupling element. Between the actuator and the coupling element, a gear mechanism can be arranged which can have bevel wheels and/or crown wheels or other gear wheels, roller or the like, in order to transfer the movement of the actuator to the coupling element. A spindle can be part of the gear mechanism, and it is likewise possible to use shafts, flexible drives, joints or other gear elements to divert, slow or accelerate the movement and bring it to the desired location. Instead of a gear mechanism, a pulley, a passive drive, a flexible shaft or a cardan drive can be provided, such that a gear can be dispensed with.

The coupling element is advantageously designed as a spindle nut, such that a longitudinal slidability of the coupling element can be ensured by a rotation movement of a spindle mounted in the medial member. It is thus easily possible to move the medial member relative to the proximal member and also move the distal member relative to the medial member by a single rotational drive movement.

The coupling element, e.g. the spindle nut, can be coupled to the lever in a rotationally rigid manner, such that the lever exclusively performs a translation movement.

Attachment points for the lever are provided on the proximal member and likewise on the distal member, which attachment points lie on mutually opposite sides of a connecting plane that extends through the pivot axles of the medial member and of the distal member. Since all the members of the gripping device are connected pivotably to each other and the pivot axles are preferably arranged parallel to each other, it is possible to lay a plane through the pivot axles of the medial member and of the distal member. The distal member is articulated on the lever on one side of this plane, and the proximal member on the opposite side of the plane. In this way, by a simple translational movement, a gripping action can be performed that corresponds to the movement of a finger. The movements between the proximal member and the medial member and between the medial member and the distal member are kinematically coupled to each other. The extent of the movement, that is to say the rotation angle, that arises from a given displacement of the lever depends on the geometry of the attachment points. By shifting the attachment points, it is possible to change the transmission of the lever gear, such that different pivot angles of the distal member and of the medial member can also be achieved.

The lever is preferably designed in one piece, in order to ensure sufficient mechanical stability and simple production. If levers are arranged on both sides along the slide axis of the coupling element, a particularly symmetrical force transmission can be ensured, such that jamming of the members relative to each other can be excluded. The preferably one-piece levers are arranged on the medial member and form the outer structure of the medial member. Alternatively or in addition, provision is made that an elastic add-on element is arranged between the lever and the coupling element, in order to achieve improved resilience. The add-on element can be arranged at both ends of the lever. Alternatively or in addition, provision is also made that an add-on element is arranged between the lever and the distal member and/or the proximal member, in order to increase the resilience. The add-on element can be designed as a separate component or can be formed integrally on the lever, the coupling element and/or the distal member and/or proximal member.

The actuator, e.g. motor, is preferably arranged in the proximal member, since the proximal member generally has most space, and a rotation movement can be transmitted very easily to a spindle via a gear mechanism, for example a bevel gear or crown wheel gear, a cable drive, a cardan joint, a flexible shaft or other gear elements. It is also possible, by way of a cardan coupling, to transmit the rotation movement of an actuator, e.g. of a motor, to the medial member, in order to cause a translation movement of the coupling element. The arrangement of the motor in the proximal member has the advantage that the energy can be delivered very easily, such that the medial and distal members only contain mechanical components designed for the gripping action. Accordingly, the medial and distal members can be made lighter, as a result of which the motor itself can be made smaller. Provision can also be made that the actuator is arranged in the distal member, which has the advantage that electronic elements and/or current supply elements can be accommodated in the proximal member, which appears expedient in respect of a partial hand replacement and can also be realized in fields of application of the gripping device other than in prosthetics.

BRIEF DESCRIPTION OF THE DRAWINGS

An illustrative embodiment of the invention is explained in more detail below with reference to the attached figures, in which:

FIG. 7 shows a plan view of a gripping device;
FIG. 9 shows a detailed view of a medial member.

DETAILED DESCRIPTION

Figure 1:
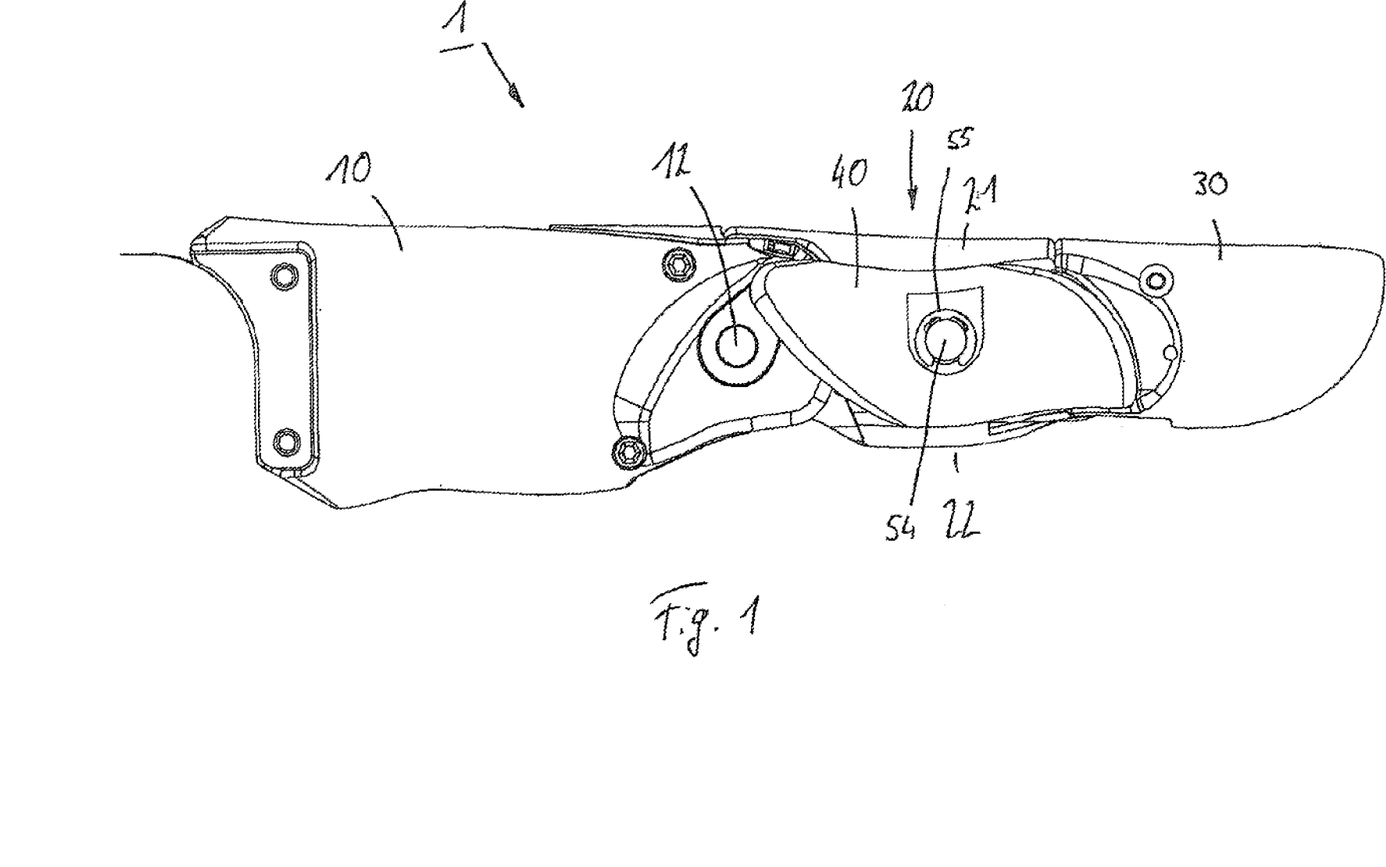
FIG. 1 shows a side view of an extended gripping device.

In FIG. 1, a gripping device 1 in the form of a prosthetic finger with a proximal member 10, a medial member 20 and a distal member 30 is shown in a side view. The proximal member 10 can be secured on a framework (not shown), being either arranged fixedly thereon or being able to be driven in an articulated manner via a drive, such that the proximal member 10 can be moved relative to the framework (not shown), similarly to a metacarpophalangeal joint.

At the distal end of the proximal member 10, the medial member 20 is mounted in an articulated manner so as to pivot about a pivot axle 12. The distal member 30 is mounted in an articulated manner on the distal end of the medial member 20. The pivot axle 23, about which the distal member 30 pivots, can be seen in FIG. 2.

The gripping device 1 is shown in an extended position in FIG. 1. Levers 40 are arranged laterally on the medial member 20, only one lever 40 being visible in the side view. An upper cover 21 and a lower cover 22 are arranged on the top and bottom of the medial member 20. A longitudinally slidable coupling mechanism, of which only the axle 54 can be seen, is arranged in the medial member 20. The lever 40 is held on the axle 54 via a spring washer 55. The levers 40 are mounted in a force-transmitting manner on the proximal member 10 and the distal member 30 and pivotably relative to the proximal member 10 and to the distal member 30 in a force-transmitting manner. The way in which they are mounted and the arrangement in which they are mounted will be explained below.

In the embodiment shown in FIG. 1, the coupling element is shown together with the levers 40 in the distal position, that is to say in the position in which the axle 54 is driven farthest in the direction of the distal member 30.

Figure 2:
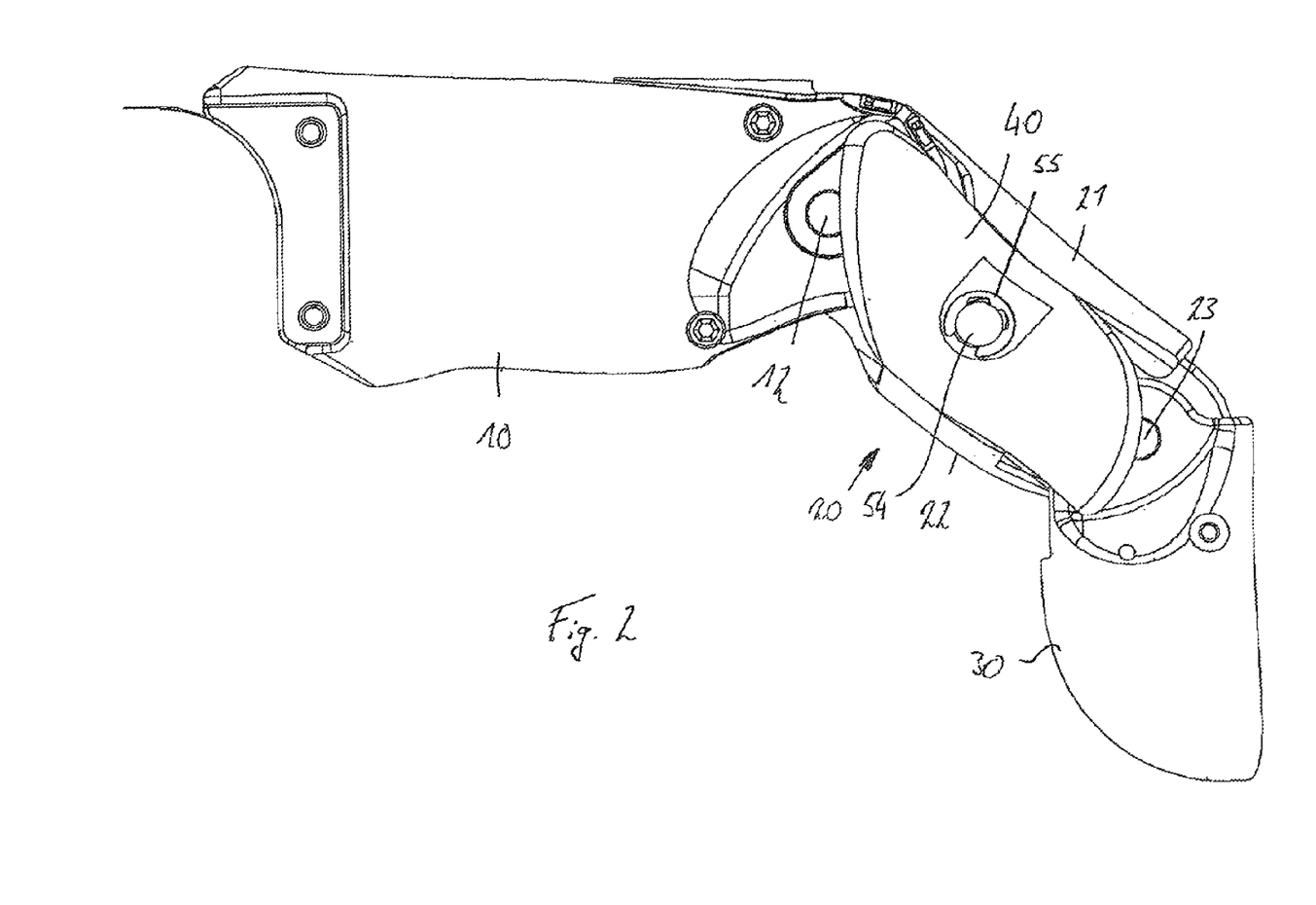
FIG. 2 shows a side view of a slightly curved gripping device.

In FIG. 2, the gripping device 1 according to FIG. 1 is shown in a slightly flexed position. The coupling element with the indicated axle 54 is driven into a central position, as a result of which the medial member 20 has been pivoted downward through approximately 45° on account of the attachment points of the levers 40 arranged diagonally to a plane between the pivot axles 12, 23. Likewise, the distal member 30 has been pivoted through approximately 45° with respect to the medial member 20, as a result of which the distal member 30 has in total been moved through approximately 90° relative to the proximal member 10. The force transmission from the coupling element to the proximal member 10 and to the distal member 30 takes place directly through the one-piece lever 40, which couples the members directly to each other.

Figure 3:
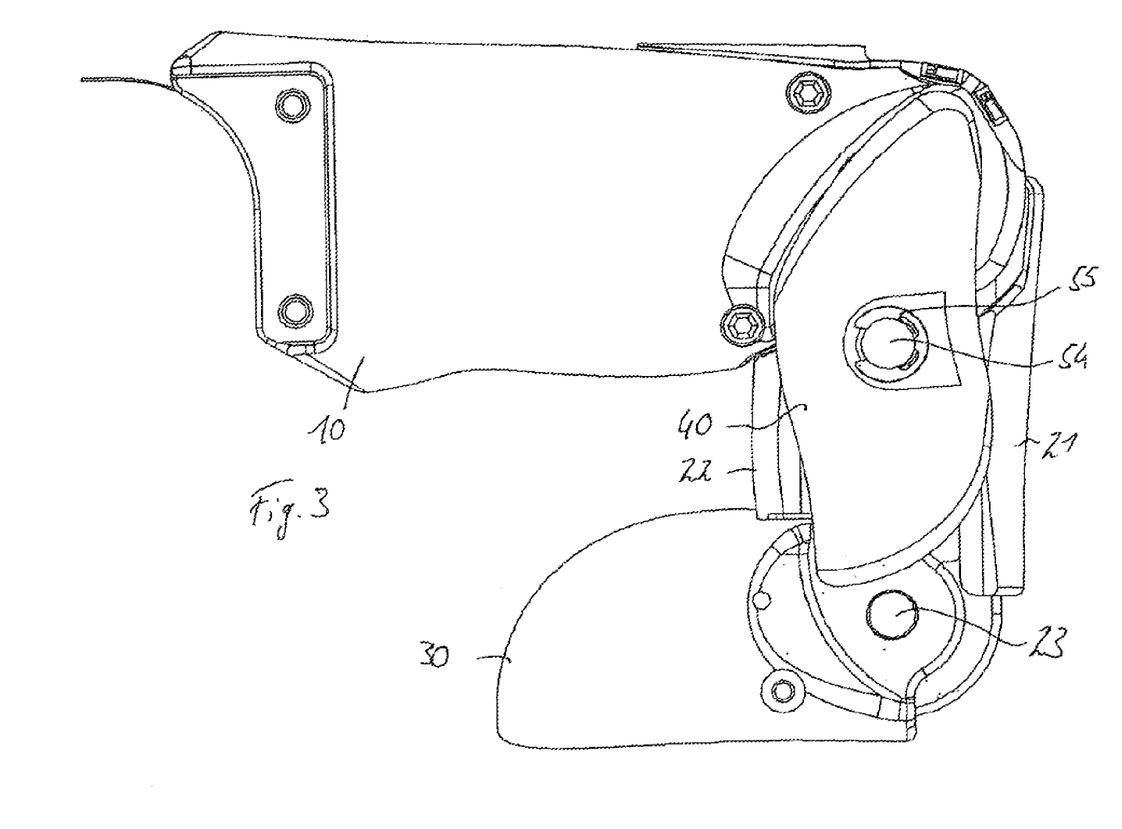
FIG. 3 shows a side view of a completely curved gripping device.

FIG. 3 shows the position of maximum flexion of the distal member 30. The axle 54 of the coupling element has been driven to the maximum extent toward the proximal member 10, the medial member 20 is approximately at a 90° angle to the proximal member 10, and the distal member 30 is at a 90° angle to the medial member 20. The position according to FIG. 3 corresponds to a maximum bend of a finger with two finger joints. The movement of displacement of the lever 40 between the positions according to FIG. 1 and FIG. 3 can be recognized from the fact that, in FIG. 1, the pivot axle 12 of the medial member relative to the proximal member 10 can be seen, whereas the originally covered pivot axle 23 of the distal member 30 relative to the medial member 20 can be seen in FIG. 3.

Figure 4:
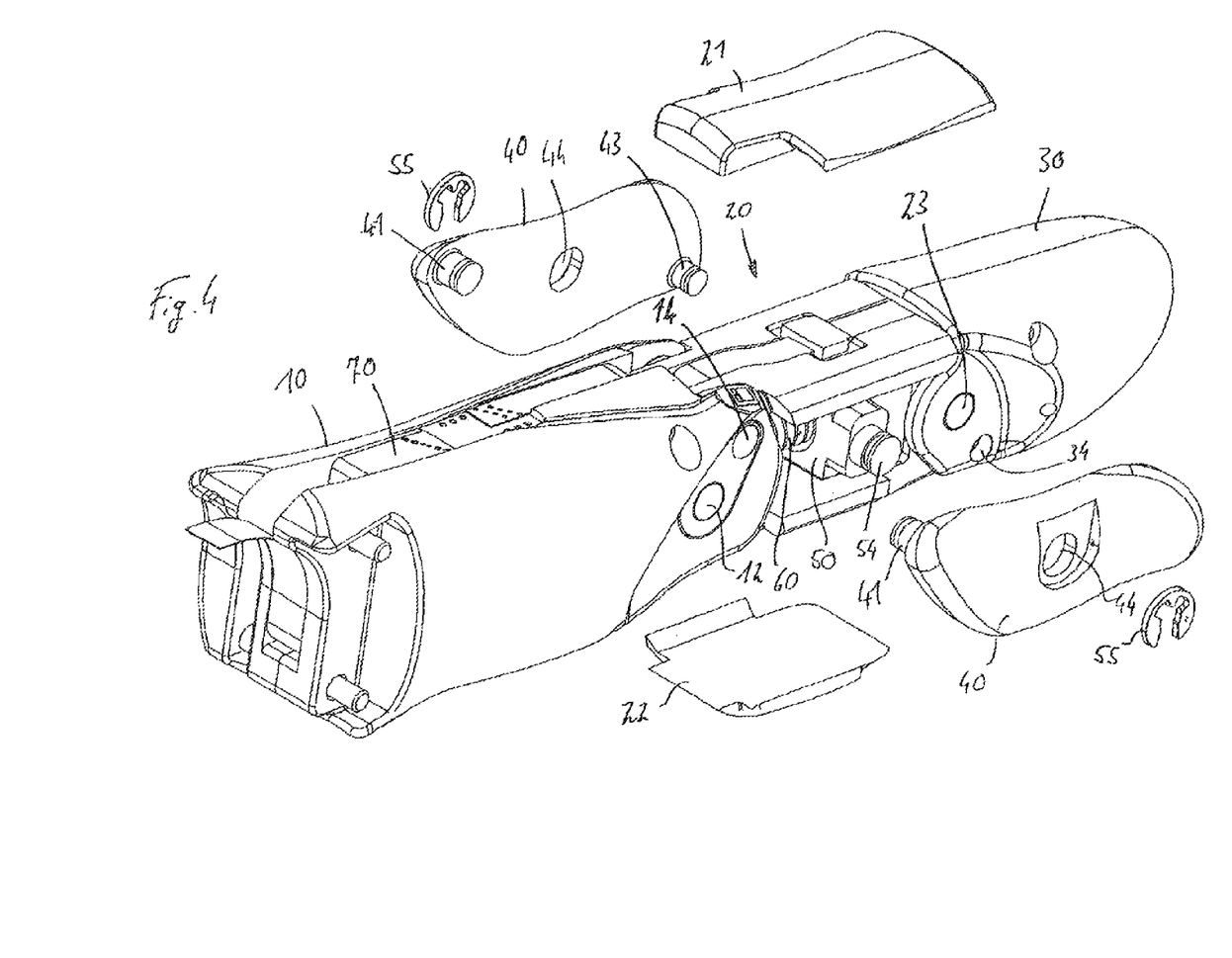
FIG. 4 shows an exploded view of an extended gripping device.

In FIG. 4, the basic structure of a gripping element 1 is shown in the form of an exploded view. A drive 70, which will be explained in more detail later, is integrated inside the proximal member 10. Above the pivot axle 12, receiving bores 14 are arranged on both sides of the longitudinal extent, that is to say on the side surfaces of the proximal member 10, and pins 41 of the levers 40 engage in these receiving bores 14. Below the plane between the two pivot axles 12, 23, a corresponding receiving bore 34 is formed on the distal member 30 and serves to receive the pin 43. Inside the levers 40, bores 44 are formed through which the axle 54 of the coupling element 50 extends. To assemble the levers 40, the pins 41, 43 must be inserted into the receiving bores 14, 34, and the axle 54 must be pushed through the bore 44 in the lever 40. The levers 40 are secured on the axle 54 by the spring washers 55, which are fitted in place from above.

A drive spindle 60, which is driven by the drive unit 70, is arranged inside the medial member 20. The drive spindle 60 is mounted rotatably and non-slidably in the medial member 20. The coupling element 50 is mounted on the drive spindle 60, and the coupling element 50 is secured against a rotation movement such that, upon rotation of the drive spindle 60, the rotation movement of the spindle 60 is converted into a translation movement of the coupling element 50, which is designed as a spindle nut.

When the spindle 60 is driven, then, depending on the direction of rotation, the coupling element 50 is moved in the direction of the proximal member 10 or of the distal member 30. In the present kinematic arrangement, a movement in the direction of the distal member 30 causes an extension of the medial member 20 and of the distal member 30, which extension ends in the position of extension according to FIG. 1. In a reverse rotation movement, the medial member 20 and the distal member 30 are pivoted about the pivot axles 12, 23 until the end position according to FIG. 3 is reached.

Figure 5:
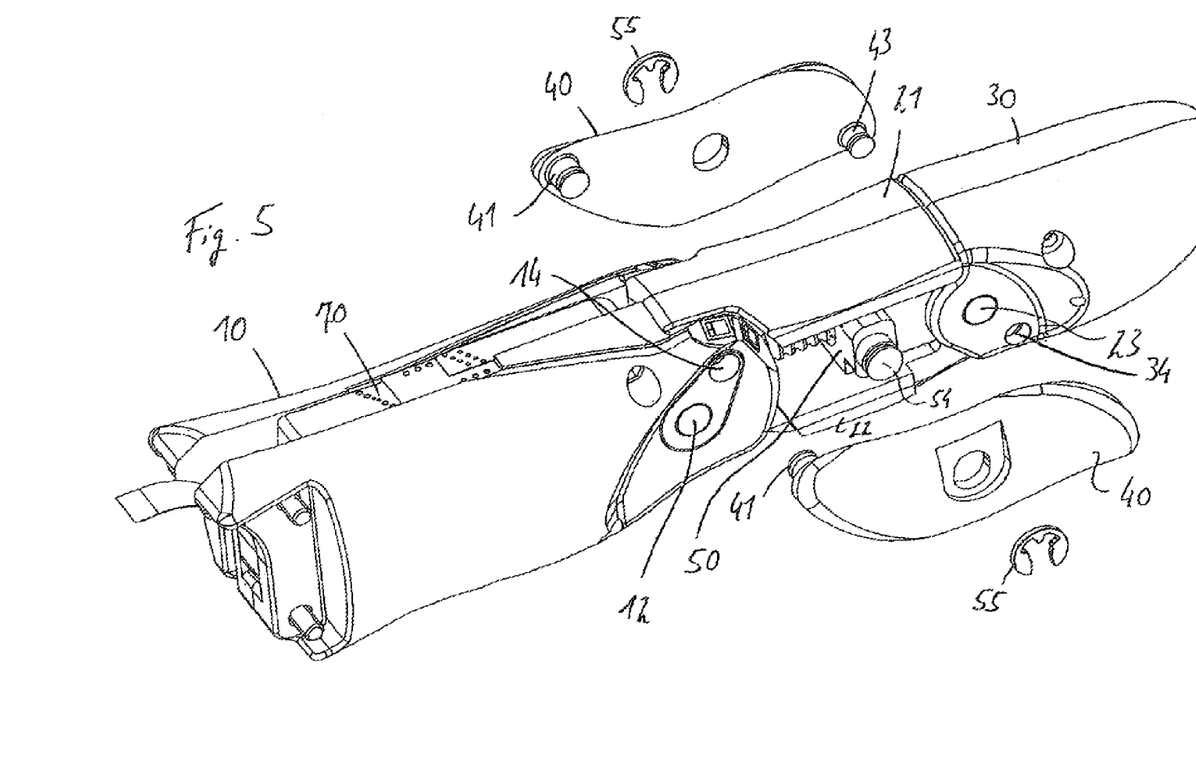
FIG. 5 shows a partially assembled gripping device.

In FIG. 5, the gripping device 1 according to FIG. 4 is shown in a partially assembled state: the upper and lower covers 21, 22 are already fitted, and the lateral levers 40 are not yet secured on the coupling element 50 and on the distal member 30 and the proximal member 10. In another arrangement of the receiving bores 14, 34, a movement of the coupling element 50 in the direction of the distal member 30 would cause a curvature, that is to say a downward bending of the distal member 30 relative to the medial member 20 and of the medial member 20 relative to the proximal member 10, while a movement in the direction of the proximal member 10 would cause an extension.

Instead of the uniform flexion illustrated, in which the medial member 20 is pivoted relative to the proximal member 10 by the same angle as the distal member 30 is pivoted relative to the medial member 20, a corresponding arrangement of the receiving bores 14, 34 can also result in a change of transmission ratio, such that different pivot angles of the individual members can be obtained from the movement of the levers 40.

Figure 6:
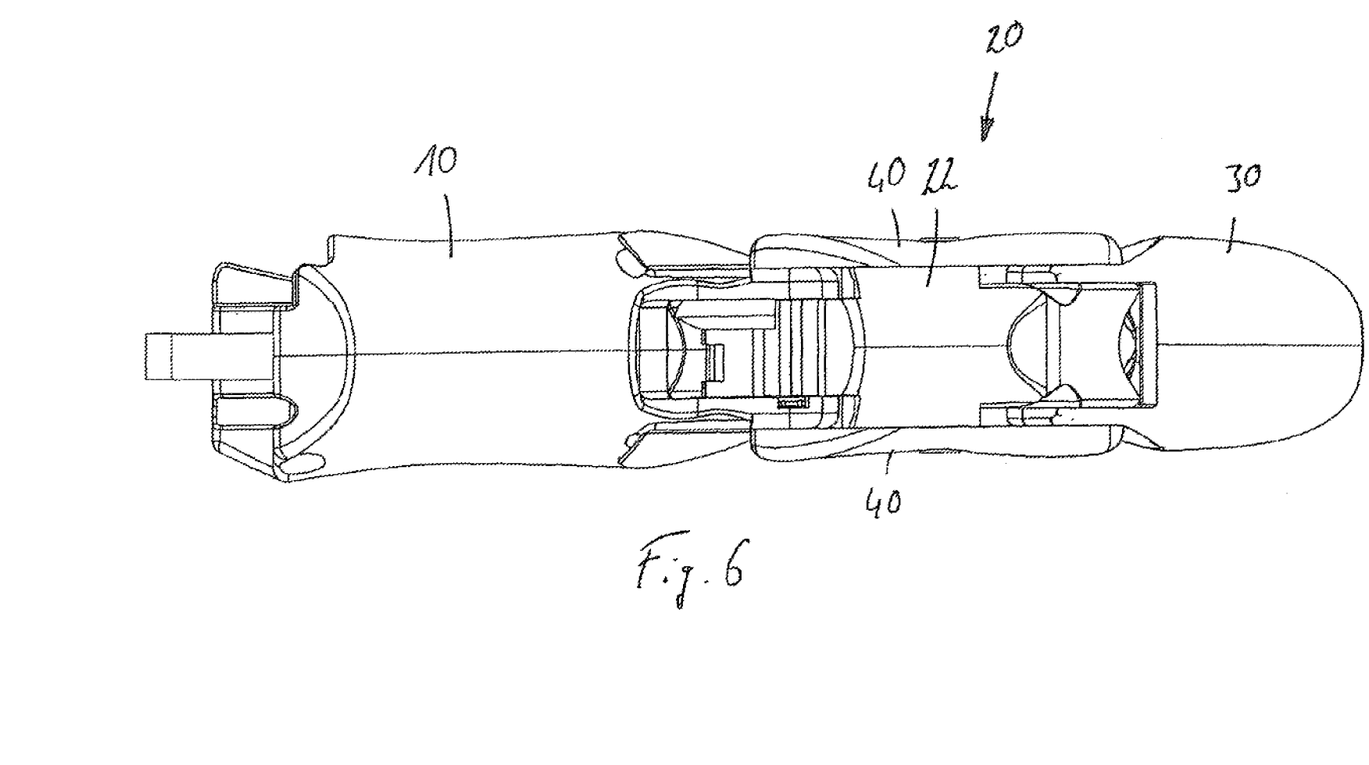
FIG. 6 shows a bottom view of a gripping device.

In FIG. 6, the gripping device 1 with the individual members 10, 20, 30 is shown in a bottom view. The two levers 40 are mounted on the medial member 20, on both sides along the longitudinal extent of the gripping device, and the lower cover 22 is likewise arranged in order to protect the drive mechanism with the spindle 60 and the coupling element 50. The coupling element 50 and the drive spindle 60 are designed as movement gears, wherein a rotation of the coupling element 50 is prevented mainly by the axles 54 being fixed in the through-bores 44 of the levers 40, since the levers 40 are coupled in a rotationally fixed manner to the proximal member 10 and to the distal member 30 via the pins 41, 43.

FIG. 7 shows a plan view of the gripping device. Here, the fixing of the levers 40 on the axles 54 by means of the spring washers 55 can be clearly seen. This figure also shows that the proximal member 10 and the distal member 30 are divided in the longitudinal extent in order to permit easier assembly.

Figure 8:
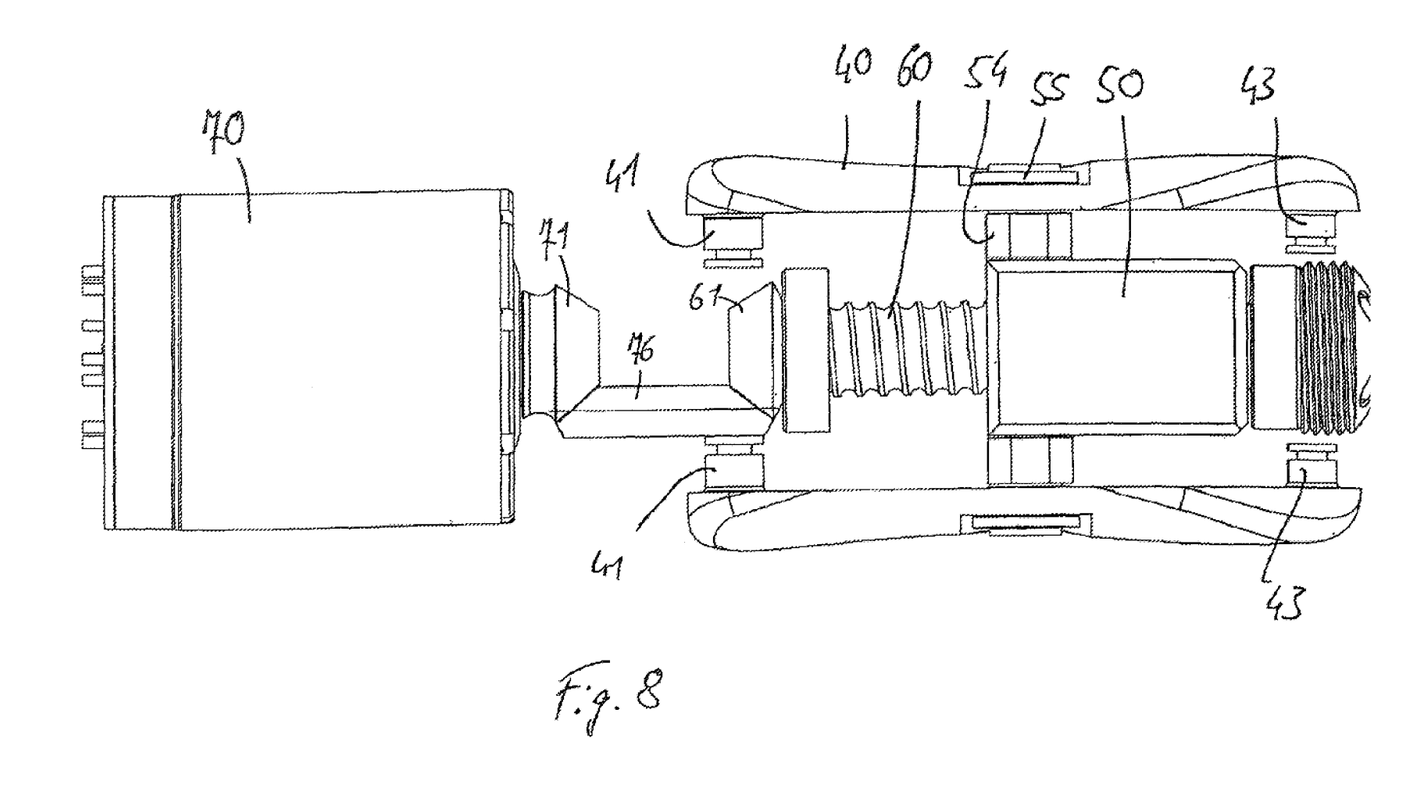
FIG. 8 shows a detailed view of the drive with force transmission mechanisms.

FIG. 8 shows the components that are needed for the movement of the members of the gripping device 1. The drive unit 70 has an actuator (not shown), in the form of a motor, and a gear on whose output shaft a driving gear wheel 71 is arranged, which is designed as a bevel wheel. The driving bevel wheel 71 is rotated in one or other direction, depending on the direction of rotation of the motor, and transmits the driving torque via a transfer gear wheel 76, which is mounted concentrically about the rotation axle 12, to the bevel wheel 61, which is assigned to the driving spindle 60 and which is coupled in a rotationally fixed manner to the spindle 60. The spindle 60 is mounted rotatably and non-slidably such that, upon rotation of the spindle 60, the coupling element 50 arranged thereon is moved in the direction of the bevel wheel 61 or moved away from the latter. Depending on the direction of movement of the coupling element 50, the two levers 40, which are connected to the coupling element 50 via the axles 54, and therefore also the pins 41, 43 are shifted in one or other direction and thereby cause a pivoting movement of the medial member 20 relative to the proximal member 10 and at the same time of the distal member 30 relative to the medial member 20.

FIG. 9 shows a view of the medial member 20 on its own, with the mounted spindle 60, and with the coupling element 50 arranged on the latter. All around the rotation axle 12, a circular recess can be seen into which the transfer gear wheel 76 can be introduced. The transfer gear wheel 76 is mounted on a bearing shoulder 120 of the axle 12 and merely has to be placed onto the axle 12 to come into engagement with the bevel wheel 61. The axle 12 can be formed in one piece with the rest of the frame of the medial member 20, likewise the distal axle 23.

To assemble the gripping device, the longitudinally divided components of the distal member 30 and of the proximal member 10 are placed onto the axles 23, 12 and fixed, and similarly the levers 40 are inserted into the receiving recesses 14, 34, together with the insertion of the axle 54 into the through-opening 44. The mechanical coupling is completed in this way. The design permits simple assembly by means of a constant joining direction of the individual components, which simply have to be fitted on from the sides and fixed.

Figure 10:
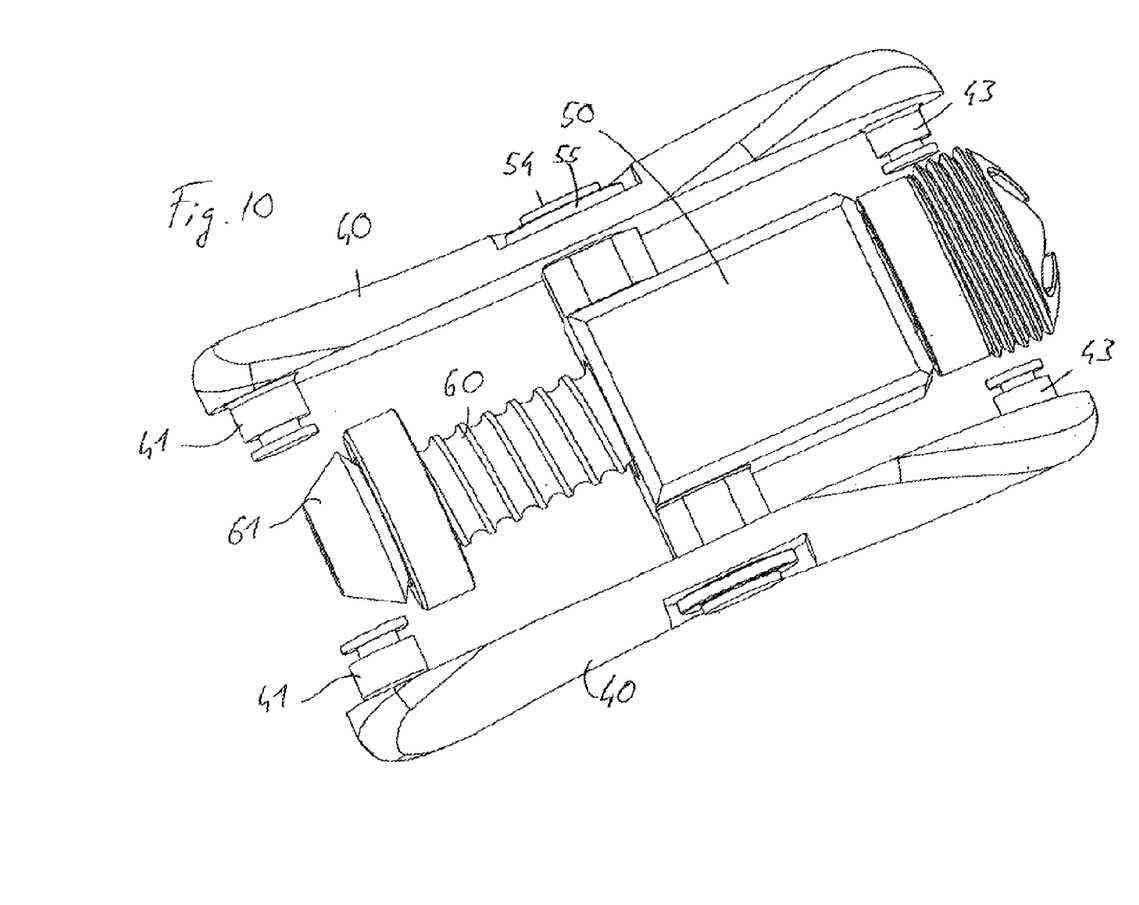
FIG. 10 shows a plan view of a medial member.

FIG. 10 shows a plan view of the force transmission mechanism. The levers 40 arranged on both sides of the coupling element 50, which is designed as a spindle nut, and the pins 41, 43 lying opposite each other can be clearly seen. At the distal end of the spindle 60, a bearing of the spindle 60 and a blocking mechanism can be seen, and the bearing and the bevel wheel 61 are arranged on the proximal end of the spindle 60.

Figure 11:
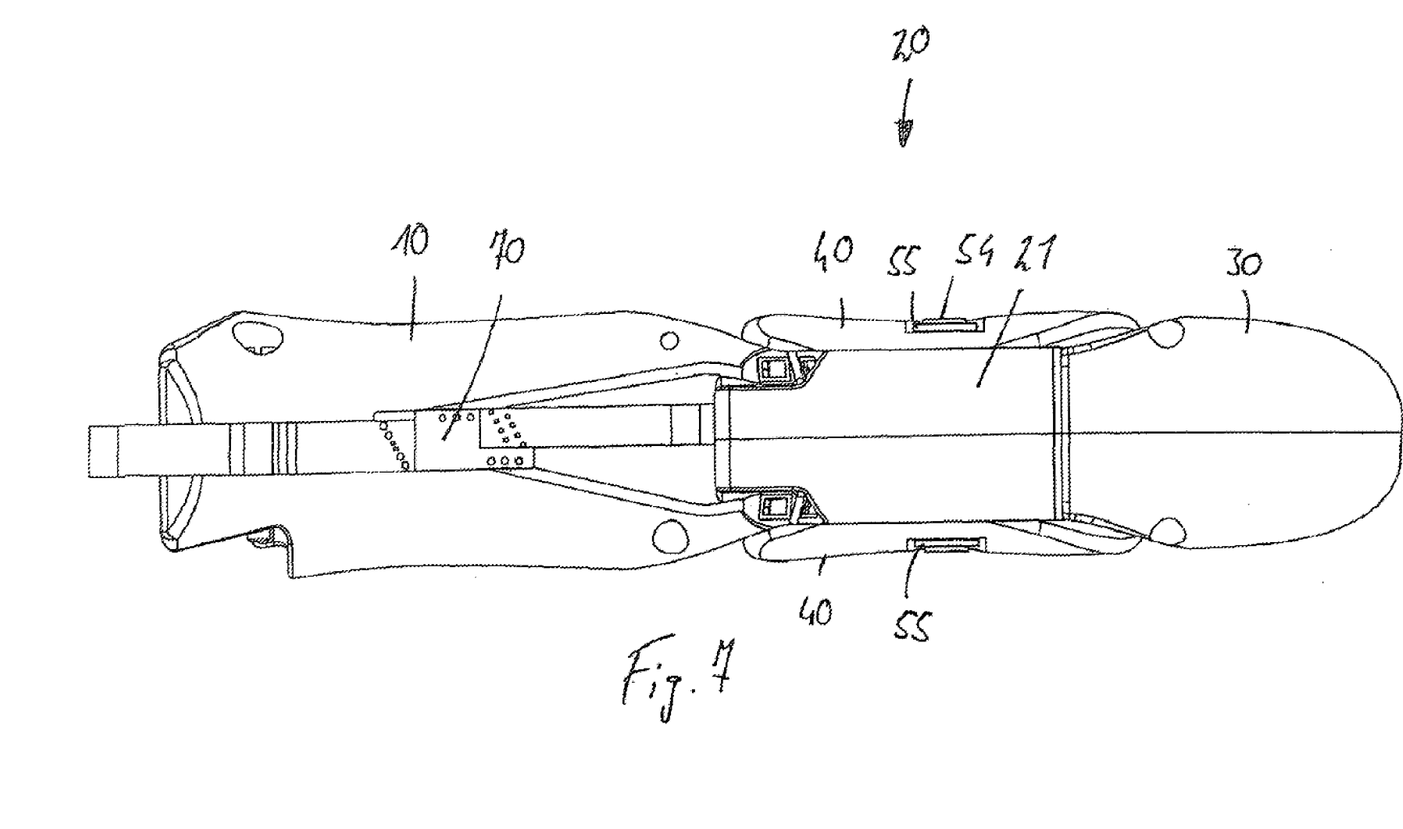
FIG. 11 shows a detailed view of a spindle and of a spindle nut.

FIG. 11 shows a detailed view of the spindle 60 with the coupling element 50 and with the axles 54 formed integrally on the coupling element 50. The bevel wheel 61 is securely screwed on the spindle 60, the proximal bearing is arranged between the bevel wheel 61 and the movement thread of the spindle 60, and the distal bearing is arranged on the end of the spindle 60 that is remote from the bevel wheel 61 and has the blocking mechanism.

Figure 12:
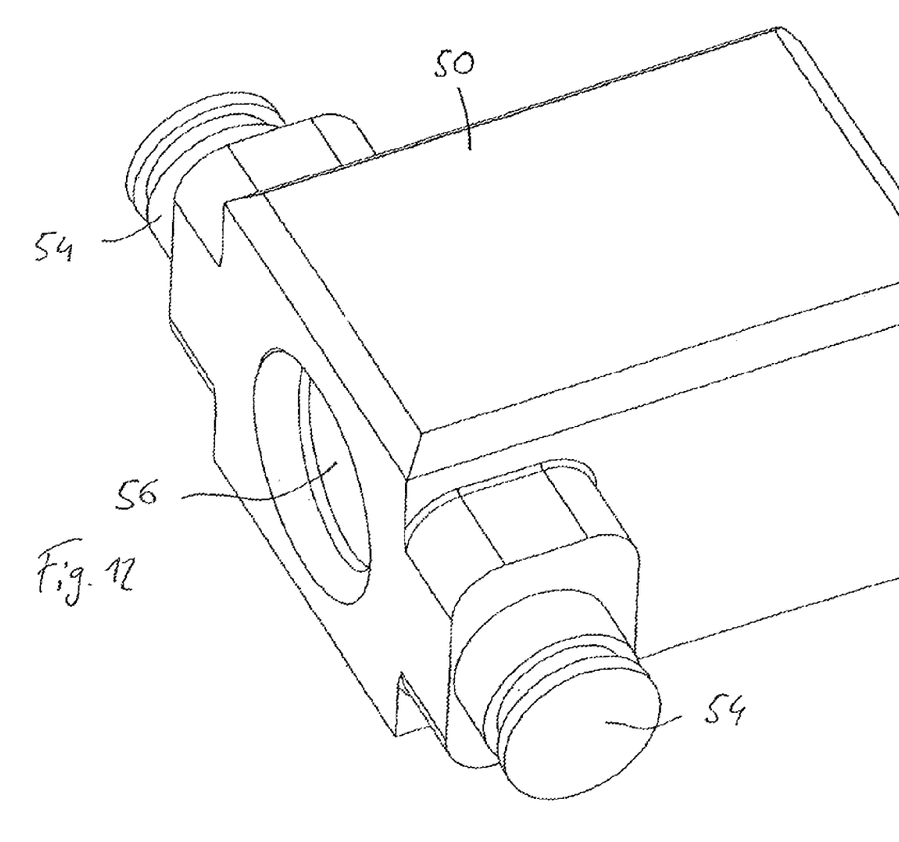
FIG. 12 shows a detailed view of a spindle nut.

FIG. 12 shows the coupling element 50 in a detailed view. The internal thread 56 is designed as a movement thread, and it is likewise possible for a recirculating ball thread to be present, in which balls circulate in the movement thread of the spindle 60 and then circulate inside the coupling element 50. It is thereby possible to operate the gripping device 1 with very low friction.

Figure 13:
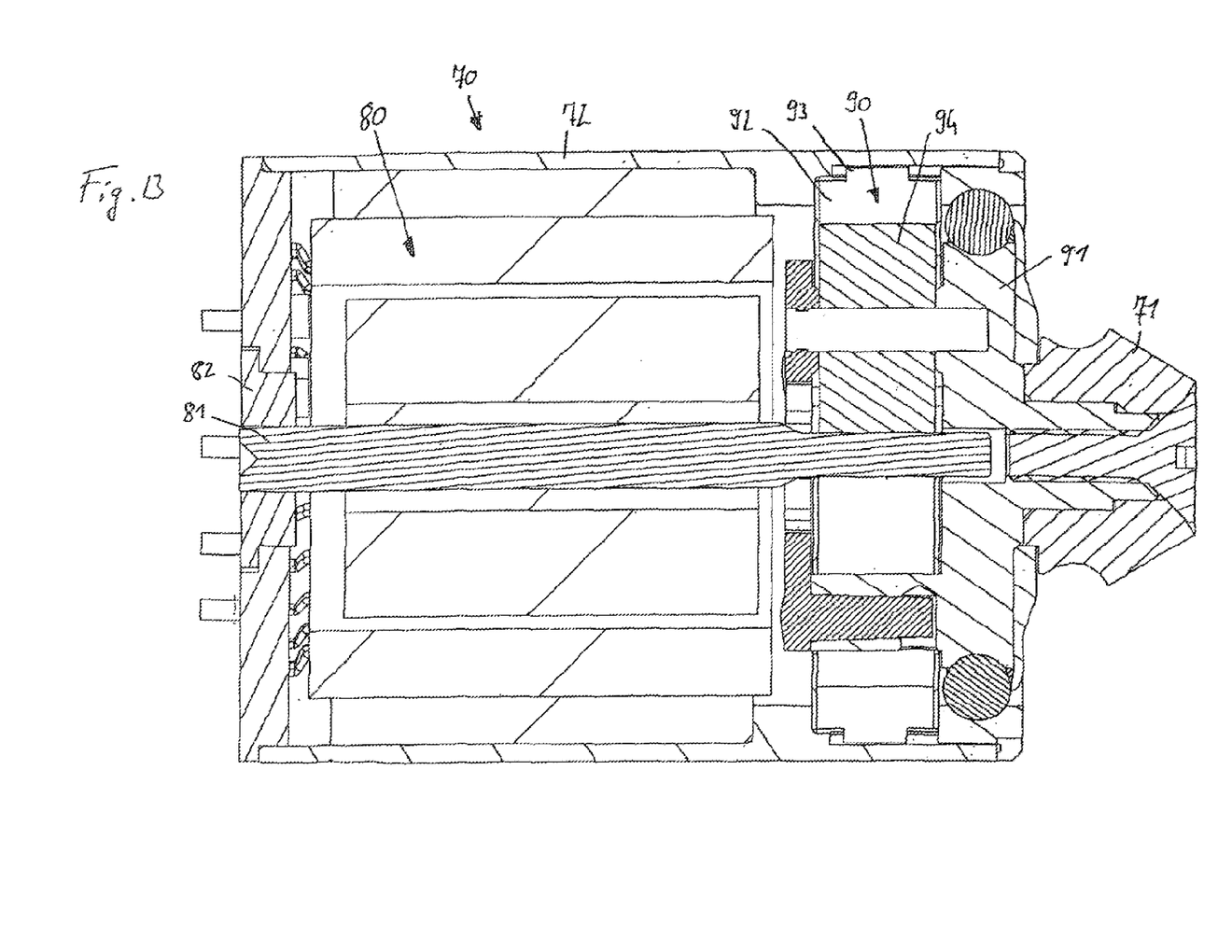
FIG. 13 shows a cross-sectional view through the drive mechanism.
Figure 14:
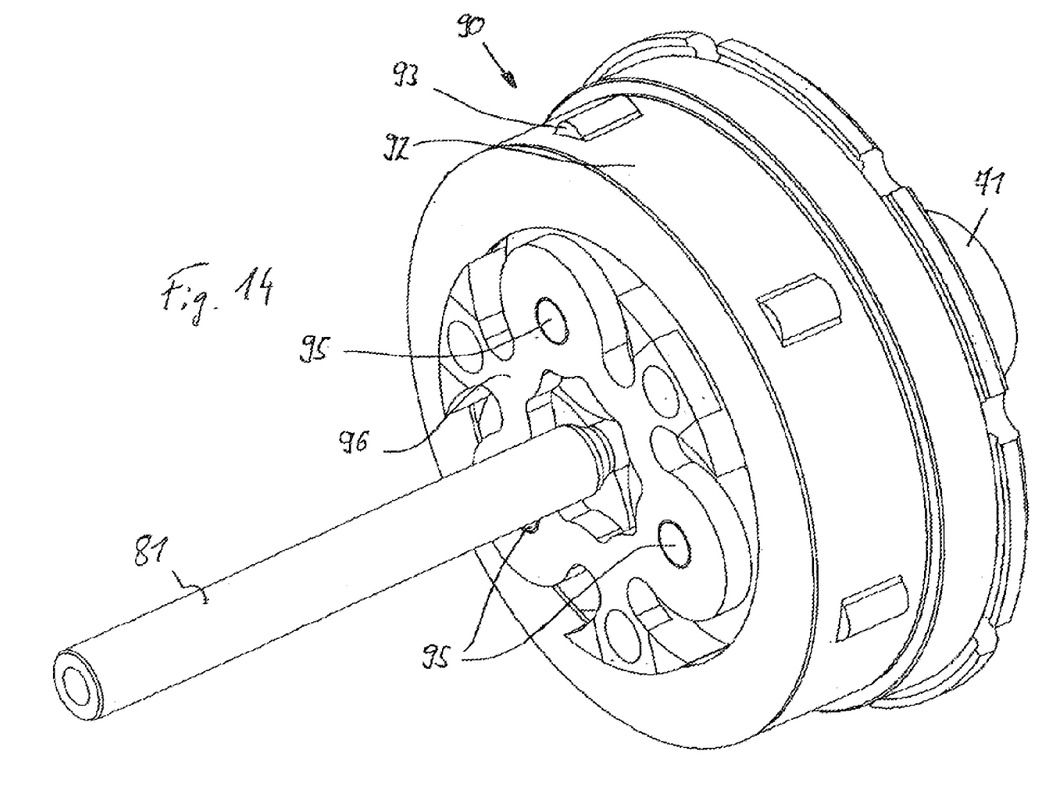
FIG. 14 shows a detailed view of a friction gear.

FIG. 13 shows a cross-sectional view of the drive unit 70, which is arranged in the proximal member 10, and the drive unit 70 has a motor 80 as actuator and a friction gear 90, which are arranged in the common housing 72. The motor 80 has an output shaft 81, which is mounted proximally on a slide bearing or ball bearing 82 and is mounted distally in the friction gear 90. The friction gear 90 is mounted on a bearing disk 91, on which the output gear wheel 71 in the form of a bevel wheel is mounted in a rotationally fixed manner. The drive power applied by the motor 80 is transferred to the output gear wheel 71 via the friction gear 90 and the bearing disk 91. The friction gear 90 has a raceway 92, on the outside of which projections 93 are formed which engage in corresponding recesses inside the housing 72, such that the raceway 92 is arranged in a rotationally fixed manner in the housing 72. Friction wheels 94 run inside the raceway 92 and are mounted on axles 95 on a bearing cage 96, as can be seen from FIG. 14.

The invention claimed is:

1. A gripping device, comprising a proximal member, a medial member, and a distal member, which are mounted pivotably on each other, and comprising an actuator, which is coupled to a slidably mounted coupling element, the coupling element being arranged between the proximal member and the distal member and being connected to the proximal member and to the distal member in a force-transmitting manner, wherein at least one lever is arranged on the coupling element, which lever connects both to the proximal member and also to the distal member, kinematically couples the proximal member to the distal member, and forms a portion of an outermost structure of the medial member that encloses internal components of the medial member.

2. The gripping device as claimed in claim 1, wherein the actuator is coupled to the coupling element via a gear mechanism.

3. The gripping device as claimed in claim 2, wherein the gear mechanism has a bevel gear or crown wheel gear and at least one of a spindle, a cable, a flexible shaft and a cardan joint.

4. The gripping device as claimed in claim 1, wherein the coupling element is designed as a spindle nut.

5. The gripping device as claimed in claim 1, wherein the coupling element is coupled to the lever in a rotationally rigid manner.

6. The gripping device as claimed in claim 1, wherein attachment points for the lever are provided on the proximal member and on the distal member, which attachment points lie on mutually opposite sides of a connecting plane that extends through the pivot axles of the medial member and of the distal member.

7. The gripping device as claimed in claim 1, wherein the lever is designed in one piece.

8. The gripping device as claimed in claim 1, wherein an elastic add-on element is arranged between the lever and at least one of the coupling element, the proximal member, and the distal member.

9. The gripping device as claimed in claim 1, wherein the lever includes first and second lever members arranged on the medial member on opposite sides along a slide axis of the coupling element.

10. The gripping device as claimed in claim 1, wherein the actuator is arranged in the proximal member or in the distal member.

11. The gripping device as claimed in claim 1, wherein the actuator is designed as a motor.

12. A gripping device, comprising:
a proximal member;
a medial member;
a distal member;
a coupling element arranged between the proximal and distal members, the coupling element being connected to the proximal member and to the distal member in a force-transmitting manner;
at least one lever pivotally connected to the coupling element and being connected to the proximal and distal members to kinematically couple the proximal member to the distal member, the at least one lever forming a portion of an outermost structure of the medial member that encloses internal components of the medial member;
wherein the medial member is interposed between and pivotally connected to the proximal and distal members.

13. The gripping device as claimed in claim 12, further comprising an actuator coupled to the coupling element via a gear mechanism.

14. The gripping device as claimed in claim 13, wherein the actuator is arranged in the proximal member or in the distal member.

15. The gripping device as claimed in claim 12, wherein the coupling element is designed as a spindle nut.

16. The gripping device as claimed in claim 12, wherein the coupling element is coupled to the lever in a rotationally rigid manner.

17. The gripping device as claimed in claim 12, wherein attachment points for the lever are provided on the proximal member and on the distal member, which attachment points lie on mutually opposite sides of a connecting plane that extends through the pivot axles of the medial member and of the distal member.

18. The gripping device as claimed in claim 12, wherein the lever is designed in one piece.

19. The gripping device as claimed in claim 12, wherein an elastic add-on element is arranged between the lever and at least one of the coupling element, the proximal member, and the distal member.

20. The gripping device as claimed in claim 12, wherein the lever includes first and second lever members arranged on the medial member on opposite sides along a slide axis of the coupling element.

* * * * *